United States Patent
Ziemba et al.

[11] Patent Number: 5,913,844
[45] Date of Patent: Jun. 22, 1999

[54] POWER INJECTOR AND METHOD PROVIDING REMOVAL OF USED DISPOSABLE SYRINGE

[75] Inventors: Robert J. Ziemba, Cincinnati; Frank M. Fago, Mason; Charles Neer, Cincinnati, all of Ohio

[73] Assignee: Liebel-Flarsheim Company, Cincinnati, Ohio

[21] Appl. No.: 08/877,083

[22] Filed: Jun. 17, 1997

[51] Int. Cl.[6] .................................................. A61M 37/00
[52] U.S. Cl. ........................................... 604/154; 604/131
[58] Field of Search .................................... 604/154, 131, 604/151, 152; 128/655, DIG. 1; 222/326, 327, 390

[56] References Cited

U.S. PATENT DOCUMENTS

| | | |
|---|---|---|
| 3,623,474 | 11/1971 | Heilman et al. . |
| 4,695,271 | 9/1987 | Goethel . |
| 4,869,720 | 9/1989 | Chernack . |
| 5,279,569 | 1/1994 | Neer et al. . |
| 5,300,031 | 4/1994 | Neer et al. . |
| 5,383,858 | 1/1995 | Reilly et al. . |
| 5,520,653 | 5/1996 | Reilly et al. . |

*Primary Examiner*—Wynn Wood Coggins
*Assistant Examiner*—N. Kent Gring
*Attorney, Agent, or Firm*—Wood, Herron & Evans, L.L.P.

[57] ABSTRACT

A power injector is provided for injecting fluid from a replaceable syringe and through an injection tube into the body of an animal. The syringe includes one or more operator-removable and interchangeable syringe mounting heads, at least one of which mounts syringes of a rear loadable type. Preferably an alternative head is provided that accepts front loadable syringes. The mounting head includes an opening and a moveable syringe holder that preferably pivots open to receive a syringe from the back of the holder and pivots closed to orient the rear of the syringe over the ram. The holder has a slot therethrough having a width sufficient to permit an injection tube attached to the syringe nozzle to be moved transversely through the slot to permit the syringe to be removed from the holder without disconnecting the tube from the orifice of the syringe and without withdrawing the tip of the tube rearwardly through the opening. The holder preferably includes a replaceable insert configured to snugly support a rear loadable syringe of a given configuration. One insert is preferably provided in the form of a pressure sleeve configured to support a syringe during high pressure use. The head has a locking mechanism that locks the syringe to the injector, couples the syringe plunger to the ram, locks and releases the head and locks the holder in operating position.

10 Claims, 2 Drawing Sheets

POWER INJECTOR AND METHOD PROVIDING REMOVAL OF USED DISPOSABLE SYRINGE

This invention relates to power injectors, particularly those of the breach loading type, and more particularly to the provision for the removal of spent replacement syringes and associated tubing from such injectors.

BACKGROUND OF THE INVENTION

Power injectors are devices used to inject fluids at controlled and programmed rates or pressures into patients. Important uses include computed tomography (CT) and angiography, where radiopaque contrast medium is injected into a patient's vascular system to enhance diagnostic images. With power injectors, a motor-driven ram advances the plunger of a syringe under microprocessor control to provide control of injection parameters such as flow rate, volume and timing. Such injectors are often loaded with sterile empty syringes that are filled by drawing fluid from a supply into the syringe through the syringe nozzle by using the ram to draw the syringe plunger backward. In other situations, the injectors are loaded with prefilled syringes. In either case, the syringes used are typically disposed of after a single use.

In CT and angiography, a typical fluid delivery system includes a power injector loaded with a single use disposable syringe that is filled with the contrast medium or other fluid, and with a delivery tube connecting the nozzle of the syringe to the vascular system of the patient. The tubing, which is also typically single-use and disposable, is commonly connected to the syringe after the syringe is loaded into the injector. When the use of the syringe and tubing is completed, the spent syringe and the tubing are removed from the injector and disposed of. Spent syringes as well as the used tubing has the capability of dripping or leaking residual amounts of fluid. This dripping or leaking can fall upon the injector components, particularly the syringe holding structure and locking mechanism, where, if not cleaned, can cause contamination or interfere with the injector operation. Cleaning of the injector of spilled fluid is time consuming, detracts from the utilization of the equipment and is accordingly costly.

In the prior art, many injectors have been configured to support syringes that are loaded into holder structure on the injector from the rear. Such syringes are typically provided with rear end flanges by which the syringes are locked to the holder and held in position for the injector ram to be coupled to and drive the syringe plunger. The loading and unloading of such rear loading syringes has required the insertion and withdrawal of the syringe nozzle through a circular opening in a closed annular holder. Upon loading, when no tubing is connected to the syringe nozzle, inserting the nozzle through the opening from the rear presents little problem. However, removal of a spent syringe from such an injector has resulted either in the withdrawal of an entire length of tubing through the opening, possibly with its leading end open to drip fluid that remains in the tube on the injector parts, or in the need to disconnect the tubing from the syringe nozzle and the withdrawal of the open nozzle end through the opening, which also can drip fluid onto the injector parts. Capping the syringe or the tubing end and the wiping of excess drippage undesirably increases the handling involved and is an inconvenience. The act of disconnecting the tubing from the syringe also occupies the hands of an operator and can result in the release of residual fluid that can require a further clean-up task.

Inventors of the subject matter of the present application have previously solved the above problem for certain types of syringes by providing a front loading injector. A front loading injector is one in which a front loadable syringe is positioned in front of an opening in an injector holder and loaded into the holder by translating the syringe rearwardly, back end first, into the injector. With front loadable injectors, the nozzle of the syringe need not pass through the opening of the holder upon loading or unloading. Such an injector, which is described and illustrated in U.S. Pat. No. 5,279,569, which is assigned to the assignee of the present application, enables an operator to remove the syringe from the injector by translating it forwardly away from the injector, without removing connected injection tubing from the syringe nozzle. This configuration has resulted in the maintenance of the injector free from fluid contamination, and has provided easier injector usage, while saving operator and physician time.

However, not all syringes, and particularly not all prefilled syringes, can be easily made available in forms that can be loaded into injectors from the front. As a result, breach loading or rear loading injector holders are still provided for many applications. Rear loading injectors are injectors in which a rear loadable syringe is positioned behind a holder of the injector and translated, nozzle first through an opening in the holder until structure on the syringe, usually a flange or other outwardly extending element at the syringe rear, seats forwardly against the holder. Usually the holder opens for loading or unloading of a syringe by pivoting away from the injector housing, either in hinged or turret fashion. Such breach loading injectors still present the above described problems in connection with the removing of spent syringes and the connected tubing.

Breach loading injectors have existed in the prior art that are modified versions of the injector disclosed in U.S. Pat. No. 5,279,569, referred to above, with the syringe holding head structure replaced with a breach loading syringe holder that pivots out of the path of the ram so that a rear loading syringe can be loaded or unloaded from the rear of the holder. Such injectors have nonetheless possessed the same disadvantages in removing spent syringe and injection tubing assemblies possessed by other breach loading injectors of the prior art.

Accordingly, there remains a need for improvement in the removal of spent syringe and injection tubing assemblies from power injectors and to eliminate the handling and equipment contamination problems that have been characteristic of the prior art rear loading power injectors available for angiographic and computed tomography.

SUMMARY OF THE INVENTION

It is a primary objective of the present invention to facilitate the removal of spent disposable syringe and of syringe and tubing combinations from power injectors. It is a particular objective of the present invention to improve the handling of spent disposable rear-loadable syringes and the injection tubing used therewith in power injectors and to reduce the likelihood of spillage or leakage of residual injection fluid when removing syringes and injection tubing from breach loading power injectors. It is a particular objective of the present invention to provide for the leak-free and easy handling and removal of used disposable rear loadable syringes without the need to disconnect the tubing from the syringe and without the need to pull the full length of the tubing through the syringe holder.

According to the principles of the present invention, a syringe holder having a syringe receiving opening or cavity therein is provided with a slotted rim through which injection tubing can be laterally passed in an outward direction when removing a syringe and tubing assembly from the syringe holder of a breach loading power injector. The invention is particularly applicable to rear loading or breach loading injectors where rear loadable syringes are loaded and unloaded from the rear of a holder having an opening therein. In loading, the nozzle of the syringe is located behind the holder and is the first part of the syringe to enter the opening as the syringe is translated axially forward into the opening until seating against the holder. Preferably, substantially the entire length of the syringe passes into the opening until the syringe seats against the holder, preferably by the contact of a flange or other extending structure at the rear of the syringe engaging the rear of the holder from the back. In unloading, the syringe is translated axially rearwardly until the body thereof is behind the holder and out of the opening, preferably with the nozzle thereof fully outside of the opening and rearward of the holder.

According to the preferred embodiment of the present invention, a syringe holder is pivotally attached to the front of a power injector. The holder pivots between an operating position and a loading position, preferably about an axis that is tangent to the circumference of the holder. In its operating position a syringe held in the holder is aligned with a power driven ram of the injector such that the ram can contact and couple to the plunger of the syringe through an opening at the back of the syringe. In the loading position, a syringe can be inserted into an opening or cavity in the holder from the back of the holder so that structure on the syringe, such as a supporting, aligning and retaining flange on the rear thereof or other structure at the syringe front end, can be engaged by structure on the syringe, for example on the holder, to lock and orient the syringe on the injector. The holder has a slot on one side of the opening or cavity that extends along the entire axial length of the holder, which permits the transverse passage of an intermediate section or length injection tubing therethrough so that the syringe can be loaded into the opening and removed from the opening of the holder while the rear end of the injection tubing remains connected to the nozzle of the syringe and the front end of the injection tubing may still be connected to fluid delivery devices, remains in the vicinity of the patient or is otherwise prevented from being withdrawn rearwardly through the opening of the holder.

In the preferred embodiment of the invention, the holder is removable, replaceable or exchangeable with holders of other configurations that are provided for supporting syringes of differing shapes or types. The holder may include an insert or sleeve that forms a replaceable inner lining to the rim of the holder and has a cooperating portion of the slot extending therethrough. Preferably, however, the holder is formed of integral or non-removeable parts the entirety of which are exchangeable to accommodate different syringes. Alternative holders include simple support rings that are configured to receive flanges and other rear end structure on syringes of differing types, while others may be in the form of or include pressure restraining jackets having slots extending the lengths thereof to similarly allow the injection tubing to be passed to facilitate the unloading of the syringe from the injector.

In further preferred embodiments of the invention, the holder is connected to a one of several alternative removable syringe support heads that may be interchangeable with heads to support other rear loadable syringes or syringes of the front loading type. The holder is preferably permanently connected to a head and replaceable therewith. The head may include coding structure such as configurations of one or more magnets that are read by sensors such as hall effect devices on the injector to provide information of the size and shape of the syringe to the controls of the injector. The use of two magnets, one with possible two values and the other with three possible values, yielding six discrete combinations, is preferred.

With the present invention, breach loadable syringes, particularly prefilled syringes having various configurations of flanges at the rear ends thereof, may be loaded into and removed from the power injectors while the injection tubing remains connected. In the removal of such syringes particularly, leakage and dripping of fluid onto injector components is avoided. Syringes can be removed from the injectors without the need to disconnect the injection tube from the syringe and without the need to pull the tip of the tube rearwardly through the holder opening.

These and other objectives of the present invention will be readily apparent from the following detailed description of the present invention in which:

BRIEF DESCRIPTION OF THE DRAWINGS

FIG. 1A is a perspective view, similar to FIG. 1, of the front end of a power injector having a breach loadable syringe mounting head and an alternative syringe holder according to further principles of the present invention, which incorporates a pressure jacket intimately surrounding the syringe.

DETAILED DESCRIPTION OF THE PREFERRED EMBODIMENTS

Figure 1:
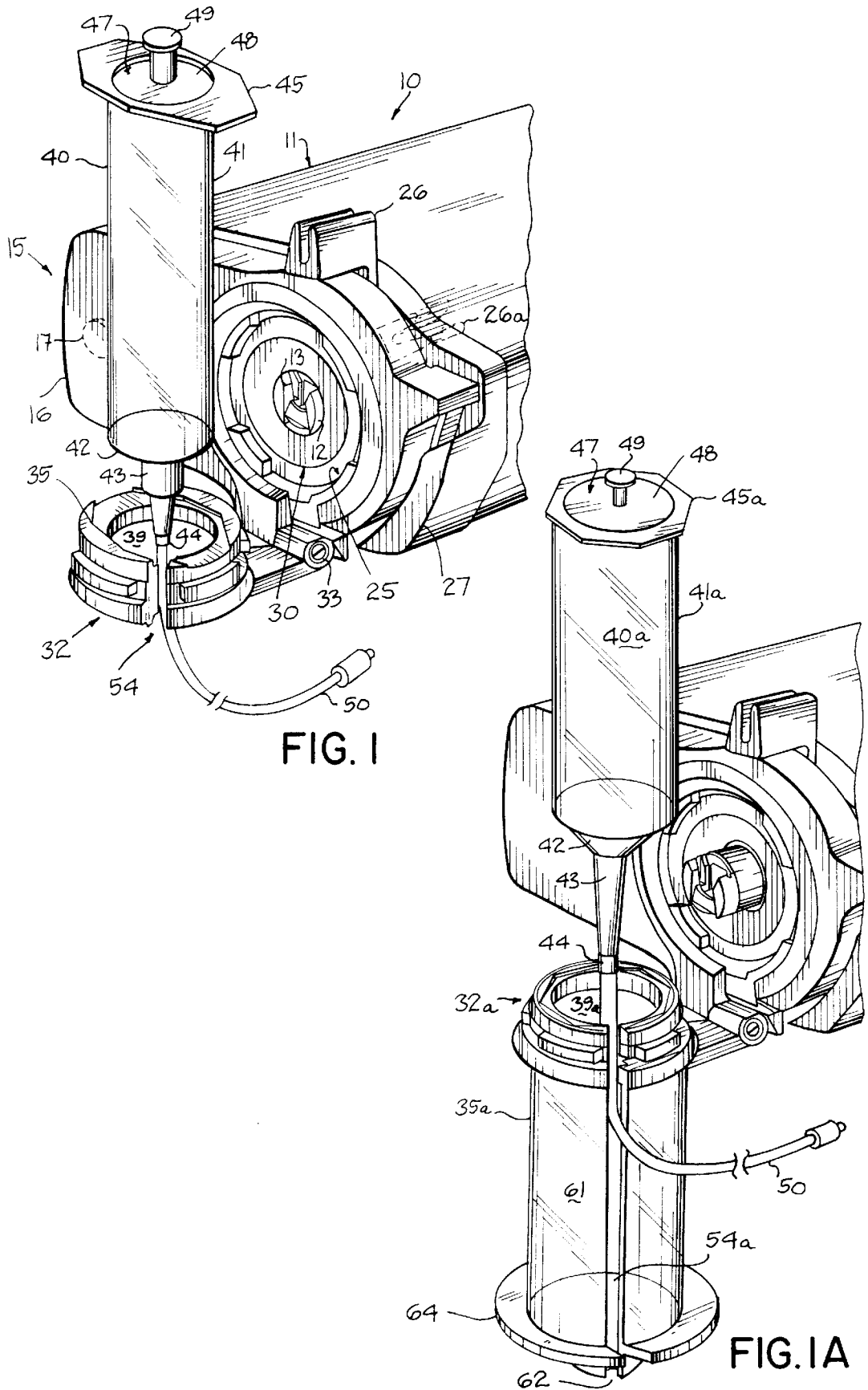
FIG. 1 is a perspective view of the front end of a power injector having a breach loadable syringe mounting head and syringe holder according to principles of the present invention, which does not incorporate a pressure jacket intimately surrounding the syringe.

FIG. 1 illustrates the front end of a power head or injection module portion of a power injector 10 of a type, for example, that is used for angiographic and CT injection. One such injector is described and illustrated in U.S. Pat. No. 5,279,569, which is assigned to the assignee of the present invention, and is expressly incorporated herein by reference herein. The injector 10 includes a injection module housing 11 that contains a power driven ram 12. The ram 12 is longitudinally moveable by activation of a motor (not shown), contained in the housing 11, so that free end 13 of the ram 12 is extendable from a retracted position inside the housing 11, as illustrated in FIG. 1, to an extended position away from the housing 11, as more fully explained in the incorporated patent. The injector of U.S. Pat. No. 5,279,569 is described in that patent as having a door assembly that constitutes a syringe mounting head of a front loading type, that is, of a type in which a syringe can be loaded by translating it rearwardly, back end first, into the front of the mounting head.

Figure 2:
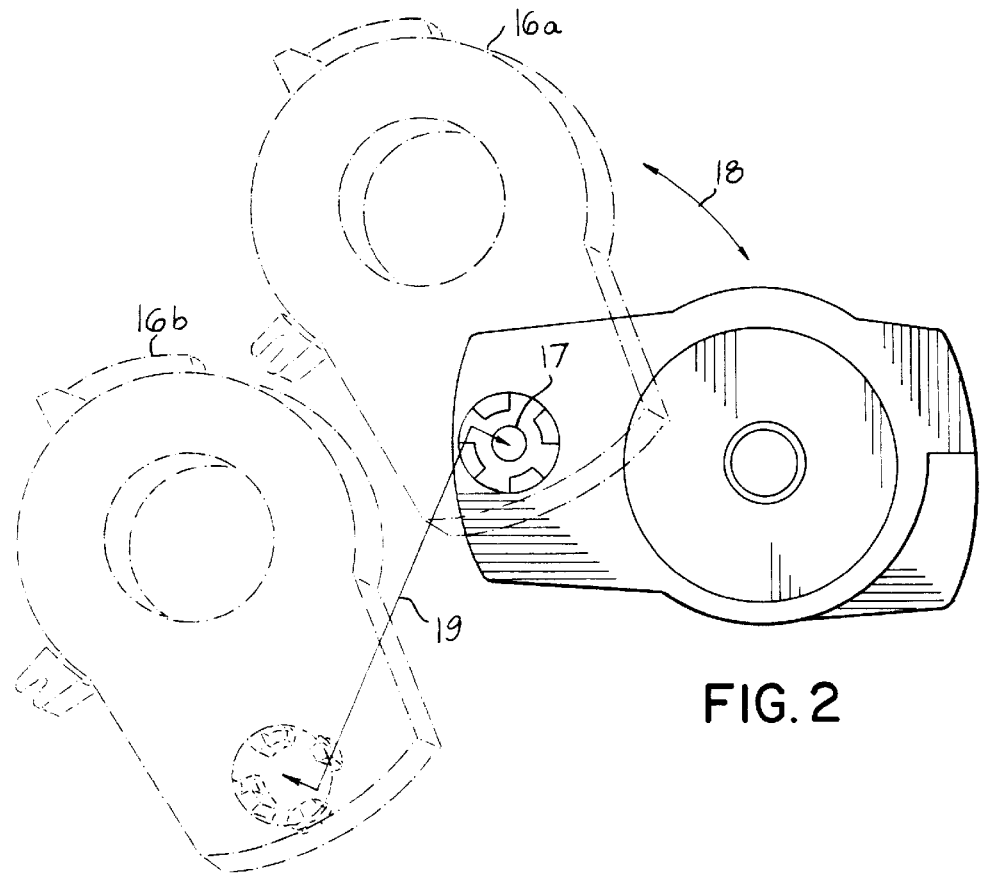
FIG. 2 is a perspective diagram illustrating the positions of the mounting head of the injectors of FIGS. 1 and 1A.

The embodiment of the invention illustrated in FIG. 1 of this application is, however, equipped with a syringe mounting head 15 that is an alternative to the front loadable head described in the patent. The mounting head 15 is rather of the breach loading or rear loading type. The head 15 includes a mounting head base 16, which is pivotally connected to the front of the housing 11 to pivot, as illustrated by the arcuate arrow 18, about a longitudinal shaft 17 to pivot between a closed position, in which the head base 16 is illustrated in FIG. 1, and an open position illustrated by the phantom line 16a of FIG. 2. In its open position 16a, the head base 16 can be translated longitudinally between the open position 16a and a removed position which is represented by the phantom lines 16b, for removal and replacement of the head 15, as illustrated by the arrow 19.

As further illustrated in FIG. 1, the head 15 is provided with a locking mechanism 25 which has several functions including the function of locking and unlocking of the head 15 to and from the housing 11 as well as additional functions described more fully below. The mechanism 25 is provided with an operating lever 26, illustrated in an unlocked or load position, which is the position which allows the head 16 to be opened, removed and replaced, as was described in connection with FIG. 2 above, and which allows syringes to be loaded and unloaded from the mounting head 15. The lever 26 is moveable to a locked position 26a, represented by phantom lines in FIG. 1, which is the position at which the ram 12 is operable to drive the plunger of a syringe mounted in the head 15. Movement of the lever 26 from its unlocked position to its locked position 26a causes the head 16 to pivot downward into engagement with a latch 27, securely locking the head 16 in its closed position. To perform the locking motion of the head 15, the locking mechanism 25 may employ any suitable structure, but preferably has that structure illustrated and described in detail in U.S. Pat. No. 5,279,569 referred to above.

Figures 3, 3A:
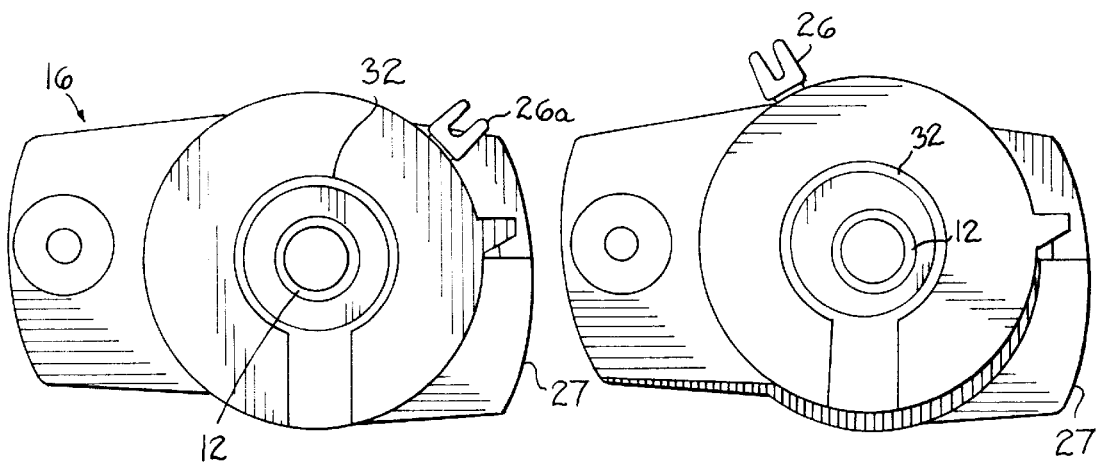
FIG. 3 is a front view of the injector of FIGS. 1 and 1A showing the head alignment when the locking mechanism is in an unlocked condition.
FIG. 3A is a front view, similar to FIG. 3, showing the head alignment when the locking mechanism is in a locked condition.

The head base 16 has a generally circular opening 30 therethrough when the lever 26 is in the load or unlocked position and the locking mechanism 25 is unlocked. With the lever 26 in this unlocked position, the center of the opening 30 is slightly to the side of, and out of alignment with, the centerline of the ram 12, as illustrated in FIG. 3. When the head 15 is in its closed position and the locking mechanism 25 is locked, the opening 30 is centered on and in alignment with the ram 12, as illustrated in FIG. 3A. Pivotally mounted to the base 16 of the head 15 on a shaft 33 adjacent the opening 30 is an annular syringe holder 32,32a. The holder 32,32a is pivotally mounted to move to an operating position in which the holder 32,32a is centered in the opening 30, as illustrated in FIGS. 3 and 3A. Movement of the lever 26 to its locked position locks the holder 32,32a in this operating position within the opening 30. When the lever 26 is in its unlocked position, the holder 32,32a is free to pivot on the shaft 33 between its operating position to its loading position, which is that illustrated in FIGS. 1 and 1A.

The holder 32,32a includes a syringe adapter sleeve 35 or 35a which is preferably an integral or permanent part thereof, but may also be one of a plurality of interchangeable adapter sleeves which fit snugly within the interior of the holder 32,32a. The adapter sleeves 35,35a are preferably are each differently configured to accept and securely support a syringe of one of several shapes in a syringe receiving opening 39,39a in the center of the holder 32,32a. Syringes of the types supported by the illustrated holders 32 and 32a are rear loading syringes, such as syringes 40 and 40a that are respectively illustrated in FIGS. 1 and 1A. The syringes 40,40a each include a tubular body 41,41 a that is generally cylindrical, a generally frusto-conical front wall 42 terminating in an elongated neck 43 having a discharge orifice 44 therethrough and locking structure generally in the form of an outwardly extending flange, such as the double winged flange 45 of the syringe 40 or the octagonal flange 45a of the syringe 40a. The body 41,41a, front wall 42, neck 43 and flange 45,45a are typically integrally molded from a plastic material which is usually transparent or translucent. Adapter sleeve 35 of the embodiment of FIG. 1 is configured to receive the double winged flange 45 of the syringe 40 and to secure it against rotation in the sleeve 35, while the sleeve 35a of the embodiment of FIG. 1A is configured to receive the hexagonally shaped flange 45a of the syringe 40a and to secure it against rotation in the sleeve 35a.

The syringe 40,40a has an open rearward end 47 which provides access by the ram 12 to a syringe plunger 48, usually formed of a hard rubber material that forms a slidable seal with the inside of the body 41,41a. The plunger 48 has a coupling element on the back thereof, for example in the form of a button 49, which the ram 12 is configured to engage to push or pull the plunger 48 forward or pull it backward in the syringe body 41,41a. Forward motion of the plunger 48 in the body 41,41a expels fluid at a programmed and controlled rate from the orifice 44 into a tube 50 connected to the neck 43 of the syringe 40,40a. The holder 32,32a as well as the sleeves 35,35a are provided with a radial slot 54,54a, respectively, extending therethrough and having a width that is greater than the outside diameter of the tube 50. The slot 54,54a permits the tube 50 to be translated sideways through the slot 54,54a, thereby permitting a syringe 40,40a having a tube 50 connected to the tip of the neck 43 to be removed from the holder 32,32a without disconnecting the tube 50 from the neck 43 and without pulling the tube 50 entirely through the opening 39,39a in the center of the holder 32,32a.

The holder 32 having the adapter sleeve 35 of FIG. 1 is useful for CT and other applications that involve only moderate pressures that are typically in the range of 30 to 150 psi. For angiographic and other high pressure applications, where pressures may be in the 500 to 2000 psi range, for example, the holder 32a is preferred having an adapter sleeve which is in the form of pressure jacket or sleeve 35a. With a pressure jacket sleeve 35a, the holder 32a has a tubular wall 61 that terminates in a conical front wall that conforms to the outside of the body 41 a and front wall 42 of the syringe 40a, with a hole 62 in the front thereof to permit extension of the syringe neck 43 therethrough. With the holder 32a that has the jacket 35a, the slot 54a extends the length thereof from the opening 39a in the back thereof to the hole 62. The existence of the slot 54a in the pressure jacketed holder 32a creates a reduction in the pressure resisting strength of the jacket 35a, which is offset by provision for extra reinforcing material, such as one or more integral rings 64 in jacket 35a. The slot 54a also extends through these rings 64.

A syringe 40,40a is loaded into the holder 32,32a with the holder 32,32a, the base 16 and the lever 26 in their respective loading and unlocked positions (FIGS. 1, 1A). The syringe 40,40a is inserted, front end first, through the opening 39,39a in the holder 32,32a from the back side thereof, until the flange 45,45a thereof is properly seated against the back side of the sleeve 35,35a. Then the holder 32,32a is pivoted into its operating position on the head 16, which is in its unlocked position (FIG. 3). The moving of the lever 26 to its locked position causes the locking mechanism 25 to lock the base 16 to the housing 11, as discussed above, and to lock the holder 32,32a in its operating position, also as discussed above, which locks the syringe flange 45,45a to the holder 32,32a. In addition, the locking of the locking mechanism 25, which causes the pivoting of the base 16 from its unlocked position to its locked position (FIG. 3 to FIG. 3A), also thereby causes the coupling 49 on the syringe plunger 48 to translate laterally into alignment with the ram 12. If the plunger coupling 49 is in the plane of the end of the ram 12 (which is the position of the ram 12 illustrated in FIG. 1A, where the ram 12 is slightly extended from the housing 11), this translation causes the plunger 48 to couple to the ram 12 as the plunger coupling 49 and ram 12 move into mutual engagement by the relative transverse motion. If the ram 12 is not in alignment with the plunger coupling 49 when the lever 26 is moved, the ram 12 can thereafter engage the coupling 49 by moving forwardly to snap into engagement with relative axial movement of the coupling 48 toward the ram 12. After the syringe 40,40a is so locked in the holder 32,32a, the rear end of the tubing 50 is typically connected to the tip of the neck 43 of the syringe 40,40a and the forward end of the tubing 50 is, when properly primed, connected to the body of the patient.

Removal of the syringe 40,40a from the injector 10 proceeds in the reverse, except that it is preferred that the tube 50 remain connected to the tip of the syringe 40,40a when the syringe 40, 40a is removed from the injector 10, to be disposed of along with the syringe 40,40a. Accordingly, the lever 26 is first moved from its locked to its unlocked positions (FIG. 3A to FIG. 3), whereupon the holder 32,32a is then pivoted to its loading position (FIGS. 1 and 1A). With the holder 32,32a in its loading position, the syringe 40,40a is withdrawn rearwardly from the opening 39,39a of the holder 32,32a and the tubing 50 is slipped sideways from the opening 39,39a and outwardly through the slot 54,54a, as illustrated in both FIGS. 1 and 1A.

Those skilled in the art will appreciate that the applications of the present invention herein are varied, and that the invention is described in preferred embodiments. Accordingly, additions and modifications can be made to the embodiments of the invention illustrated and described herein without departing from the principles of the invention. Therefore, what is claimed is:

1. A power injector for injecting fluid from a replaceable syringe and through an injection tube into the body of an animal, where the syringe has a plunger slidable therein and mounting structure at a rearward end thereof that is configured to retain the syringe in a holder when loaded into the holder from the back side of the holder, and where the syringe has an orifice at the front end thereof that is connectable to the back end of the injection tube, the injector comprising:

a housing;
   a power driven ram supported for reciprocal longitudinal movement on the housing and having a plunger coupling at a free end thereof for coupling to the plunger of the syringe;
   a syringe mounting head supported on the housing and operable to support a syringe, by engaging the mounting structure thereof, in an injection position at which the ram is extendable from the housing into the rearward end of the syringe to couple to the plunger and to slide the plunger longitudinally in the syringe;
   the head including a base fixed to the housing and a syringe holder having an opening therein and moveably linked to the base to move between a closed position thereon at which the syringe is in its injection position and an open position thereon at which the syringe is forwardly loadable into the opening from a rear side of the holder and is rearwardly removable from the opening to the rear side of the holder; and
   the holder having the length thereof a slot therethrough having a width sufficient to permit the tube to be moved transversely through the slot from the opening to permit the syringe to be removed from the holder without disconnecting the back end of the tube from the orifice of the syringe and without withdrawing the front end of the tube rearwardly through the opening.

2. The injector of claim 1 wherein:
the holder is pivotally attached to the head base to pivot between its closed and open position.

3. The injector of claim 1 wherein:
the holder includes a replaceable insert configured to snugly support a rear loadable syringe of a given configuration.

4. The injector of claim 3 wherein:
the insert is in the form of a pressure sleeve configured to support a syringe against outward deformation under internal fluid pressure when the syringe is loaded in the sleeve, front-end-first, from the back side of the holder; and the slot extends along the length of the sleeve.

5. The injector of claim 1 wherein:
the base includes a locking mechanism having an unlocked position at which a syringe can be loaded and unloaded to and from the holder and at which the holder is free to move between its positions and a locked position at which the holder is locked in its closed position and a syringe, when in the holder, is locked to the injector.

6. The injector of claim 5 wherein:
when the mechanism is in its locked position, the plunger of a syringe mounted in the holder is coupled to the ram and, when the mechanism is in its unlocked position, the plunger is uncoupled from the ram.

7. The injector of claim 1 wherein:
the base includes a locking mechanism having an unlocked position at which the holder is free to move between its positions, and having a locked position at which the holder is locked in its closed position.

8. The injector of claim 1 wherein:
the syringe mounting head is operator-removably supported on the housing of the injector.

9. The injector of claim 8 wherein:
the syringe mounting head is one of a plurality of operator-removable and interchangeable mounting heads, each differently configured to mount one of a plurality of differently configured syringes.

10. The injector of claim 9 wherein:
the syringe mounting heads of the plurality include at least two alternative heads, one configured to mount a syringe of a rear loadable type and one configured to mount a syringe of a front loadable type.

* * * * *

UNITED STATES PATENT AND TRADEMARK OFFICE
CERTIFICATE OF CORRECTION

PATENT NO. : 5,913,844
DATED : June 22, 1999
INVENTOR(S) : Robert J. Ziemba et al.

It is certified that error appears in the above-indentified patent and that said Letters Patent is hereby corrected as shown below:

Column 5, line 28 reads "26acauses" and should read --26a causes--.

Signed and Sealed this

Twenty-fifth Day of January, 2000

Attest:

Attesting Officer

*Acting Commissioner of Patents and Trademarks*